United States Patent [19]

Voigt et al.

[11] Patent Number: 4,504,670
[45] Date of Patent: Mar. 12, 1985

[54] PROCESS FOR THE CONTINUOUS MANUFACTURE OF TRIOXANE

[75] Inventors: Hartmut Voigt, Frankfurt am Main; Karl-Friedrich Mück, Wiesbaden; Helmut Bär, Offenbach am Main; Herbert Mader, Nauheim; Karlheinz Burg; Günter Sextro, both of Wiesbaden, all of Fed. Rep. of Germany

[73] Assignee: Hoechst Aktiengesellschaft, Frankfurt am Main, Fed. Rep. of Germany

[21] Appl. No.: 539,624

[22] Filed: Oct. 6, 1983

Related U.S. Application Data

[63] Continuation of Ser. No. 135,168, Mar. 27, 1978, abandoned.

[30] Foreign Application Priority Data

Mar. 30, 1979 [DE] Fed. Rep. of Germany ....... 2912767

[51] Int. Cl.³ .................. C07D 323/06; C07D 321/06; C07D 319/06; C07D 317/12; C07D 321/12; C07D 321/00

[52] U.S. Cl. .................. 549/347; 549/368; 549/369; 549/430

[58] Field of Search ............... 549/347, 368, 369, 430

[56] References Cited

FOREIGN PATENT DOCUMENTS

| | | |
|---|---|---|
| 1135491 | 8/1962 | Fed. Rep. of Germany ...... 260/340 |
| 1570335 | 2/1970 | Fed. Rep. of Germany ...... 260/340 |
| 2103687 | 8/1972 | Fed. Rep. of Germany ...... 260/340 |
| 1543390 | 11/1972 | Fed. Rep. of Germany ...... 260/340 |
| 2428719 | 1/1975 | Fed. Rep. of Germany ...... 260/340 |
| 1012372 | 12/1965 | United Kingdom ............... 260/340 |

OTHER PUBLICATIONS

E. Bartholome et al., Chem. Ing. Tech., vol. 43, No. 10, pp. 597–644.

Primary Examiner—Norma S. Milestone
Attorney, Agent, or Firm—Curtis, Morris & Safford

[57] ABSTRACT

The invention provides a process for the continuous manufacture of trioxan, optionally together with cyclic formals, from aqueous formaldehyde solutions in a circulation reactor with evaporator, the vapor/liquid mixture leaving the evaporator is fed in below the liquid level of the reaction mixture. The process of the invention allows to attain especially high space/time yields.

3 Claims, 1 Drawing Figure

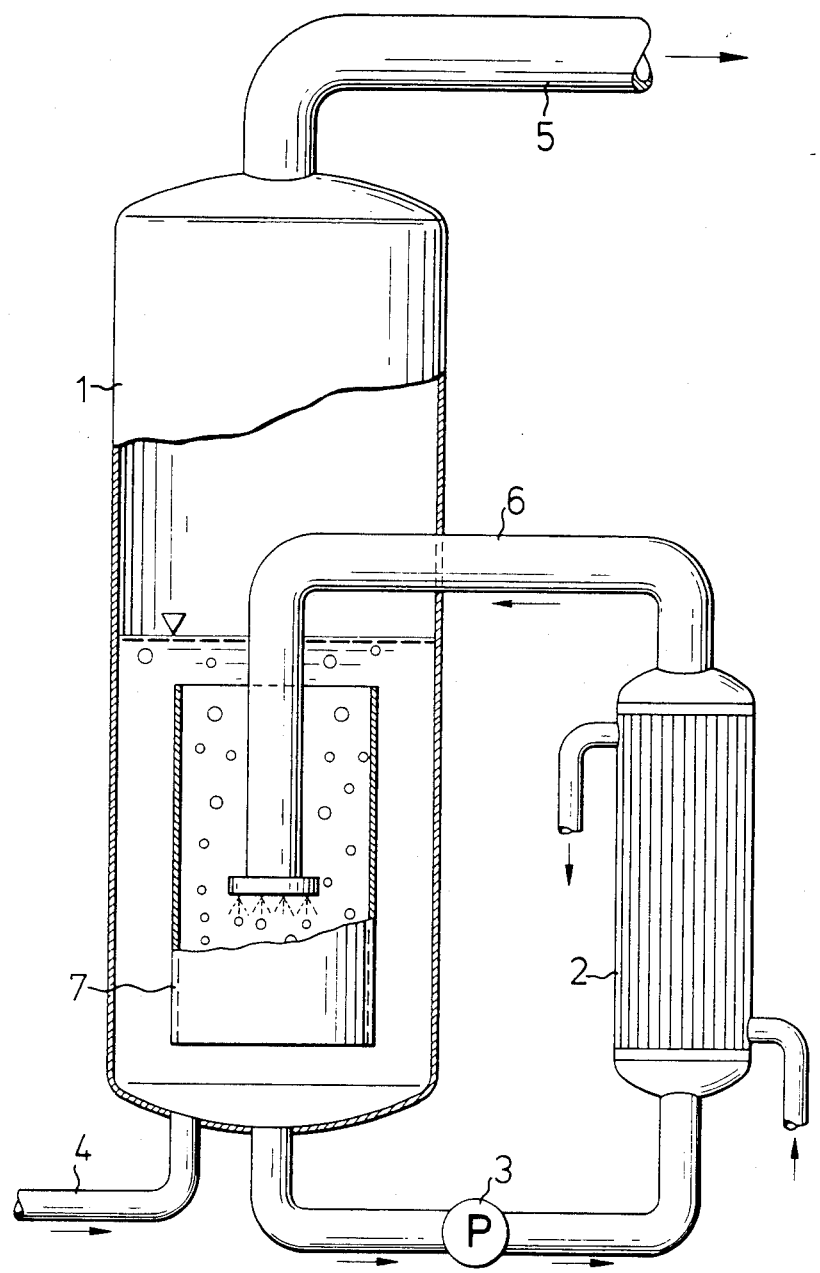

PROCESS FOR THE CONTINUOUS MANUFACTURE OF TRIOXANE

This application is a continuation of application Ser. No. 135,168, filed Mar. 27, 1978, abandoned.

The manufacture of trioxan from aqueous formaldehyde is described in the literature (see Walker, Formaldehyde, Reinhold Publ., New York, 3rd ed., 1964, pp. 198/199). The trioxan formed at elevated temperatures in the presence of acidic catalysts is separated from the reaction mixture by distillation. Generally, the synthesis vapor containing trioxan, water and formaldehyde as well as by-products of the synthesis is rectified either according to U.S. Pat. No. 2,304,080 in a rectifying column mounted onto the reactor, or according to British Pat. No. 1,012,372 in a column provided with rectifier and discharge section. The fraction rich in trioxan so obtained is further worked up by extraction and/or another known separation process.

It is known that the time yields (g of trioxan per kg of formaldehyde and hour) of trioxan synthesis are low. According to German Pat. No. 1,135,491, for example, a time yield of 152 g of trioxan per kg of formaldehyde and hour is attained by simple distillation of the reaction mixture from the reaction vessel. The low time yields cause necessarily long residence times in the manufacture of trioxan from aqueous formaldehyde solutions. Moreover, large reaction volumes are required in order to attain industrially satisfactory space/time yields (g of trioxan per liter of reaction volume and time).

In order to increase the space/time yields of trioxan synthesis, it has been proposed to distrub substantially the chemical balance of formaldehyde and trioxan in the reaction mixture by operating at high evaporation speed. However, this operation mode results in a low trioxan concentration in the synthesis vapor (see E. Bartholomé, Chem. Ing. Techn. 43, (1971) 597), the work-up of which vapors requires great energy expenditure.

In German Auslegeschrift No. 1,543,390, there is furthermore described a process for which a maximum time yield of 1090 g of trioxan per kg of formaldehyde and hour is indicated. In this process, an aqueous formaldehyde solution is heated to boiling in a circulation evaporator in the presence of acidic catalysts, and the synthesis vapors rich in trioxan are then removed via a column mounted on top of the reactor. To this column, reaction liquid being in a chemical balance is fed to meet the synthesis vapor, in order to ensure that, even at high evaporation speed, the trioxan concentration of the synthesis vapors attains the equilibrium value which generally is maintained only at low evaporation speed and which corresponds to the distribution equilibrium of trioxan in gaseous and liquid phase.

The disadvantage of the process in accordance with this German Auslegeschrift No. 1,543,390 resides in the fact that additional equipment is required, which involves considerable increase of the reactor volume and thus a decrease of the space/time yields. In the process as described, the equipment which is contacted with the reaction liquid consists therefore of the reactor as such, an evaporator, a pump, a long tubular duct, optionally with dwelling vessel, and a column. All these devices must be made from materials which resist to an acidic (for example sulfuric acid-containing) formaldehyde solution having a temperature of about 100° C. The general disadvantages of corrosion-proof reactors are described in German Auslegeschrift No. 2 103 687. When calculating the space/time yields, considerably lower values are obtained than those indicated in German Auslegeschrift No. 1,543,390.

In German Offenlegungsschrift No. 2,428,719, there is furthermore described a process for the separation of trioxan from aqueous solutions containing trioxan and formaldehyde, according to which from 5 to 15 weight % of the solutions are distilled off at temperatures of below 100° C. under reduced pressure and at a residence time of less than 1 minute, and subsequently the trioxan is isolated from the distillate. This operation mode has the disadvantage of poor time yields.

It has also been proposed to obtain high space/time yields of trioxan even at high throughout rates by adjusting the quotient of evaporated reaction mixture and reaction mixture circulating through the evaporator in a forced circulation reactor to 0.001 to 0.04. In order to make this feasible, pumps having a corresponding conveying capacity are required between reactor and evaporator.

The present invention provides a process for the continuous manufacture of trioxan from aqueous formaldehyde solutions in the presence of acidic catalysts in a circulation reactor with evaporator at a residence time of from 2 to 240 minutes, wherein the vapor/liquid mixture leaving the evaporator is fed in below the liquid level of the reaction mixture in the reactor, and the vaporous product current is let off from the reactor.

Subject of the present invention is furthermore a continuous process for the simultaneous manufacture of trioxan and cyclic formals, which comprises treating an aqueous formaldehyde solution containing at least one diol and/or at least one epoxide in the manner as described above.

According to the process of the invention, there are surprisingly obtained in the synthesis vapor trioxan concentrations corresponding to the equilibrium value, even at high evaporation speed.

The trimerization reaction of formaldehyde in order to obtain trioxan is carried out in known manner by reacting aqueous, generally 30–80%, preferably 40–70%, formaldehyde solutions, optionally with addition of known anti-foaming agents, in the presence of known acidic catalysts such as mineral acids, strong organic bases or another acidic catalyst in an amount as required for maintaining a corresponding catalytic activity. Suitable acidic catalysts, which have to be less volatile than the reaction mixture, are for example sulfuric acid, phosphoric acid, p-toluenesulfonic acid or acidic ion exchangers. The quantity is not critical and generally in a range of from 2 to 25%, preferably 2 to 10%.

When according to the above process variant of the invention a mixture of trioxan and at least one cyclic formal is to be manufactured, from 1 to 25 weight %, preferably 2 to 15 weight %, relative to formaldehyde, of at least one diol and/or at least one epoxide must be added to the aqueous formaldehyde solution.

Suitable diols for this application are above all 1,2-, 1,3- and α,ω-diols. Alternatively, the corresponding epoxides may be used instead of the 1,2-diols, or mixtures of both compounds. Preferably, diols are employed the cyclic formals of which have boiling points below 150° C. and/or, with water, form low-boiling azeotropic mixtures (<150° C.), or are volatile in steam. Suitable are for example ethyleneglycol, ethylene oxide, propyleneglycol-1,2, propylene oxide, propyleneglycol-1,3, butanediol-1,2, butanediol-1,3, butanediol-1,4, and butene(3)diol-1,2. Preferably, ethyleneglycol or ethylene oxide, propyleneglycol-1,2 and butanediol-1,4 are used in accordance with the invention, and especially ethyleneglycol or ethylene oxide.

In accordance with the invention, the reaction is carried out in a circulation reactor preferably with forced circulation, which is provided with an evaporator. Suitable are for example forced circulation evaporators consisting of reaction vessel, pump and evaporator, such as described for example in Ullmann, vol, 1 (1951), 3rd. ed., pp. 533–537. The conveying capacity of the pump is not critical, and depends substantially on the intended degree of evaporation.

The residence time of the reaction mixture in the reactor system is from 2 to 240 minutes, preferably 5 to 120 minutes, and especially 15 to 60 minutes. The temperatures of the reaction mixture are from 50° to 150° C., preferably 95° to 110° C., depending on the pressure.

The reaction product consisting of trioxan, formaldehyde and water and optionally cyclic formals is evaporated in the evaporator. Operations may be carried out under normal pressure, under reduced pressure, for example of from 150 to 950 mbars, or under elevated pressure of, for example 1 to 4 bars. Preferred is normal pressure.

The evaporation degree according to the invention (quotient of evaporated product amount and product amount circulating through the evaporator × 100) of the reaction mixture in the evaporator is for example from 0.1 to 25%, preferably 1 to 20%, and especially from 6 to 14%.

In accordance with the invention, the liquid/vapor mixture leaving the evaporator is fed to the reaction vessel below the liquid level of the reaction mixture by means of a dip pipe. This immersion in the reaction mixture should be as deep as possible in order to ensure optimal exchange of substance and optimal agitation of the reactor contents (mammoth pump principle). The immersion depth should be for example from 20 to 80%, preferably 30 to 70%, of the actual state of charge of the reactor, and immersion depth, kind and arrangement of the pump (if present) must be in such a relation that cavitation cannot occur.

In order to improve the exchange of substance between liquid and gaseous phase, and the mammoth principle, additional intermixing and gassing of the reactor charge may be ensured by installation of known separation elements (distributors) in the reactor, such as metal sheets arranged centrically around the dip pipe, preferably in cylindrical form such as shown in the accompanying drawing.

The synthesis vapor leaving the reactor system is concentrated in usual manner in vapor or condensate form by means of a rectification as described for example in British Pat. No. 1,012,372. The fraction rich in trioxan obtained which contains possibly cyclic formals can be purified, for example by extraction with a water-immiscible solvent for trioxan and possibly cyclic formals such as methylene chloride, and subsequent neutralization and fractional distillation or crystallization. Other known separation processes may alternatively be applied, such as described for example in Process Economics Program, Stanford Institute Report 23 (1967), p. 181, or German Offenlegungsschrift No. 1,570,335.

The process of the invention is especially advantageous also with respect to operational technique, because apart from, for example, a pump mounted between reactor and evaporator, an increase of the reaction zone by additional equipment is not required in order to produce a synthesis vapor having the maximum trioxan content which corresponds to the equilibrium value in the gaseous phase for the distribution balance of trioxan in liquid and gaseous phase, even at high evaporation speed. According to processes hitherto described, this trioxan content can be obtained only when operating at low evaporation speed, or according to the complicated and expensive operation mode of German Auslegeschrift No. 1,543,390. In accordance with the invention, space/time yields can be attained which are considerably superior to those resulting in accordance with the state of the art.

Furthermore, the process of the invention allows the synthesis of trioxan at a minimum energy consumption; it is thus distinguished by a favorable energy balance.

The operation mode of the invention is furthermore distinguished by the fact that the short residence times at high evaporation speed reduce the formation of by-products such as formic acid. Low catalyst acid concentrations or the use of ion exchangers have an identical effect.

The following examples illustrate the invention.

EXAMPLES

The test apparatus is shown in the accompanying drawing. The reactor consists of the vessel (1), the evaporator (2), in special cases a tubular heat exchanger, and the pump (3). Via duct (4), aqueous formaldehyde solution is after-dosed continuously. The acidic catalyst is introduced into the reaction vessel (1) together with aqueous formaldehyde solution, while the distillate is removed via duct (5). (7) is a cylindrical separating element for improved exchange of substance between liquid and gaseous phase. The liquid/vapor mixture leaving the evaporator is fed to the vessel below the liquid level via the dip pipe (6). The immersion depth of the feed pipe is 70% of the state of charge of the reactor.

1,000 g each of a mixture of 90 parts of a 63.5% aqueous formaldehyde solution and 10 parts of concentrated sulfuric acid are introduced into the reaction vessel (1), which is preheated to 95° C. The mixture is pumped through the evaporator (2) by means of the pump (3). Depending on the intended throughout, the evaporator is heated at varying temperatures. The synthesis vapor leaving the system is totally condensed in a quenching system, and the condensate is examined for its content of trioxan and formaldehyde. 63.5% Formaldehyde solution is afterdosed in amounts corresponding to the evaporated portion. The test time is 6 hours in each case. The results and those of the Comparative Tests are listed in Tables 1 2.

Examples 1 to 3 (Table 1) demonstrate that the trioxan concentrations in the synthesis vapor the independent of the evaporation degree in the evaporator.

TABLE 1

| Example No. | Trioxan in the distillate % | Evaporation degree % | Conversion rate % | Residence time h |
|---|---|---|---|---|
| 1 | 22.3 | 1.2 | 35.1 | 1.00 |
| 2 | 21.5 | 2.5 | 33.8 | 0.96 |
| 3 | 22.6 | 11.1 | 35.6 | 1.00 |

Table 2 demonstrate that, at identical residence time, the trioxan concentration in the synthesis vapor is above 20 weight % according to the process of the invention as well as in the Comparative Example (according to German Auslegeschrift No. 1,534,390). However, as compared to this latter comparative process, the process of the invention is distinguished by substantially higher space/time yields, due to the considerably reduced reaction volume.

TABLE 2

| Example No. | Formaldehyde concentration Inlet % | Residence time h | Trioxan in the distillate % | Reactor volume | Ratio of reaction volumes | Conversion to trioxan % | Ratio of space/time yields |
| --- | --- | --- | --- | --- | --- | --- | --- |
| 4 | 63.5 | 0.3 | 22.4 | reactor, evaporator, pump | 1 | 35.3 | 1 |
| 5* | 63.5 | 0.3 | 20.8 | reactor, pump, evaporator, column, long tubular duct | 1.5–2 | 32.8 | 0.68–0.51 |

*acc. to Example 2 of G.A.S. 1,543,390

What is claimed is:

1. A process for the continuous manufacture of trioxan, optionally together with cyclic formals, from aqueous formaldehyde solutions containing optionally at least one diol and/or at least one epoxide, in the presence of acidic catalysts, in a circulation reactor with evaporator, at a residence time in the range of from 15 to 240 minutes, wherein the vapor/liquid mixture leaving the evaporator is fed in below the liquid level of the reaction mixture in the reactor, and the vaporous product current is let off from the reactor.

2. The process as claimed in claim 1, wherein the vapor/liquid mixture leaving the evaporator is fed in at 30 to 70% below the liquid level.

3. The process as claimed in claims 1 or 2, wherein the vapor amount leaving the system is from 6 to 14%, relative to the product amount circulating through the evaporator.

* * * * *